US00PP27982P2

(12) United States Plant Patent
Doyle

(10) Patent No.: US PP27,982 P2
(45) Date of Patent: May 9, 2017

(54) FIG TREE NAMED 'S-49'

(50) Latin Name: *Ficus carica*
Varietal Denomination: S-49

(71) Applicant: James F. Doyle, Roseville, CA (US)

(72) Inventor: James F. Doyle, Roseville, CA (US)

(73) Assignee: James F. Doyle, Roseville, CA (US)

( * ) Notice: Subject to any disclaimer, the term of this patent is extended or adjusted under 35 U.S.C. 154(b) by 38 days.

(21) Appl. No.: 14/756,888

(22) Filed: Oct. 26, 2015

(51) Int. Cl.
*A01H 5/08* (2006.01)

(52) U.S. Cl.
USPC ..... Plt./211

(58) Field of Classification Search
USPC ..... Plt./211
See application file for complete search history.

*Primary Examiner* — Keith Robinson
(74) *Attorney, Agent, or Firm* — Randall Danskin P.S.

(57) ABSTRACT

A new and distinct variety of fig tree which is denominated varietally as 'S-49' is described, and which further produces an attractively colored fig which is ripe for harvesting and shipment of a second crop during late July and early August under the ecological conditions prevailing in the San Joaquin Valley of Central California.

4 Drawing Sheets

Latin name: *Ficus carica.*
Varietal denomination: S-49.

BACKGROUND OF THE NEW VARIETY

The present invention relates to a new, novel and distinct variety of fig tree and which has been denominated varietally as 'S-49', and more specifically to a novel fig tree which produces a fruit which is considered large, and red-purple in skin color, and which further has a tree growth characteristic which is considered precocious, and is additionally a productive and regular bearer of fruit. The present new variety of fig tree produces fruit which are suitable for packing and shipping as a fresh market fig, and which additionally has a fruit pulp which has an attractive, strawberry red color, a fine texture, and is further sweet and rich in flavor.

ORIGIN AND ASEXUAL REPRODUCTION OF THE NEW VARIETY

It has long been recognized that several important factors contributing to the success of any new variety of fresh fruit for sale in the fresh market is its date of harvesting and its exterior appearance, as well as its ability to be harvested later in the season thus allowing it to be brought to market at a time when other varieties are not commercially available.

The new fig tree variety 'S-49', as disclosed herein, was derived by the methodology which is set forth as follows. This new fig tree variety was the result of a controlled hybrid cross pollination made in the summer of 2010 by the Inventor. The Inventor has been involved in the development of new fig tree varieties since 1985, and has further produced and evaluated thousands of fig hybrid seedlings during the last 30 years of his professional career. The aforementioned cross-pollination involved the fig tree variety 'Desert King' [unpatented], which was used as the seed [female] parent; and the caprifig tree '91C' [unpatented], and which was used as the pollen [male] parent. The male parent caprifig Tree '91C' is an unpatented and proprietary caprifig tree which is owned by the Inventor. The genes which are resident within the caprifig tree '91C' include genes from both the fig tree 'CA Brown Turkey' [unpatented]; and the 'Calimyrna' fig tree. [unpatented]. In the development of the new variety, the fruit produced by the 'Desert King' fig tree was covered with a cloth cage prior to the time of pollen receptivity of the fruit so that insects that might cause unwanted pollination might be excluded. The cloth cage was subsequently removed during the manual pollination process, and then, immediately replaced until such a time as the fruit attained full maturity.

After attaining maturity the fruit of the previously mentioned 'Desert King' fig tree were removed, and about 500 hybrid seeds from this cross-pollination were harvested, cleaned, dried, and stored in the fall of 2010. Subsequently, about 150 seeds from this stored hybrid seed population were planted in small containers on property that I control, and which is located in Roseville, Calif., in the spring of 2011. These seeds were subsequently germinated and grew into small seedlings. Ninety-eight (98) seedlings were produced from this population, and were eventually field planted in a seedling row in the fall of 2011 at a testing area which is located near Traver, Tulare County, and in the central portion of the San Joaquin Valley of Calif. The aforementioned specific seedling population received the alpha-numeric identification numbers 'S-1' through 'S-98'. From among this family of seedlings the subject, new fig tree variety identified as 'S-49' was selected by the Inventor for further testing, and asexual reproduction. The new fig tree variety 'S-49' first fruited and was selected in August of 2013.

The new variety 'S-49' fig tree was first asexually propagated by the Inventor at Traver, Calif., in 2014, by grafting the new fig tree variety onto an existing fig tree which was approximately five years old. The new graft produced, and matured fruit during August of 2015. The fruit was subsequently evaluated. This first asexual propagation produced fruit and vegetation that appeared identical in all respects to the fruit and foliage as first seen on the original 'S-49' fig tree.

SUMMARY OF THE VARIETY

The new fig tree variety 'S-49' produces large, red-purple, to purple skinned figs of the common type. The new fig tree is characterized by a growth characteristic where the tree is of smaller than average stature, and which further displays a precocious growth habit, and is further a productive, and regular bearer of fruit. The new fig tree produces two crops, both the breba, or first crop, and the productive, second, or main crop. The fruit eye of the fruit produced by the 'S-49' fig tree is small to medium in size thereby restricting the entrance of many insects that could cause internal decay. Still further, the fruit skin and meat is moderately thick and durable. This makes the fruit very suitable for packing and shipping as a fresh-market product. In addition to the foregoing, the fruit pulp is an attractive strawberry-red color, has a fine texture, and is further considered sweet and rich in flavor. The fruit produced by the new variety of fig tree appears to hold its large size later into the season than other commercial varieties of fig trees, thus extending the season for prime size, and quality fresh figs when other fig varieties are not commonly available.

BRIEF DESCRIPTION OF THE DRAWINGS

The accompanying drawings are color photographs of the present variety of fig tree.

FIG. 3 further shows the exterior appearance of the fruit sufficiently mature for harvesting and shipment. Additionally, another fruit in FIG. 3 is shown severed in the longitudinal plane so as to display the flesh characteristics thereof.

Figure 1:
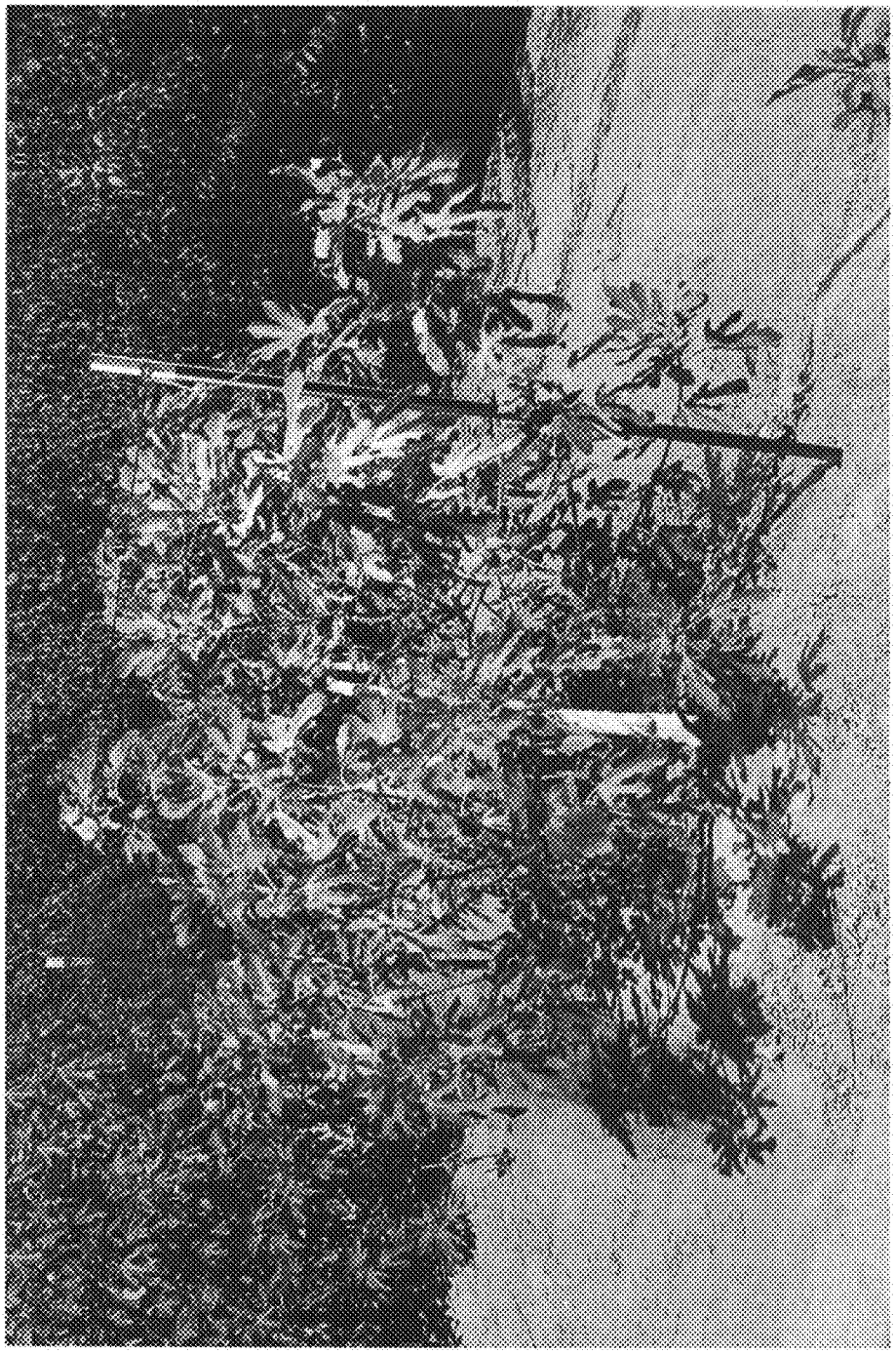
FIG. 1 depicts the original seedling tree of the present variety, and which is ripe for harvesting and shipment.
Figure 2:
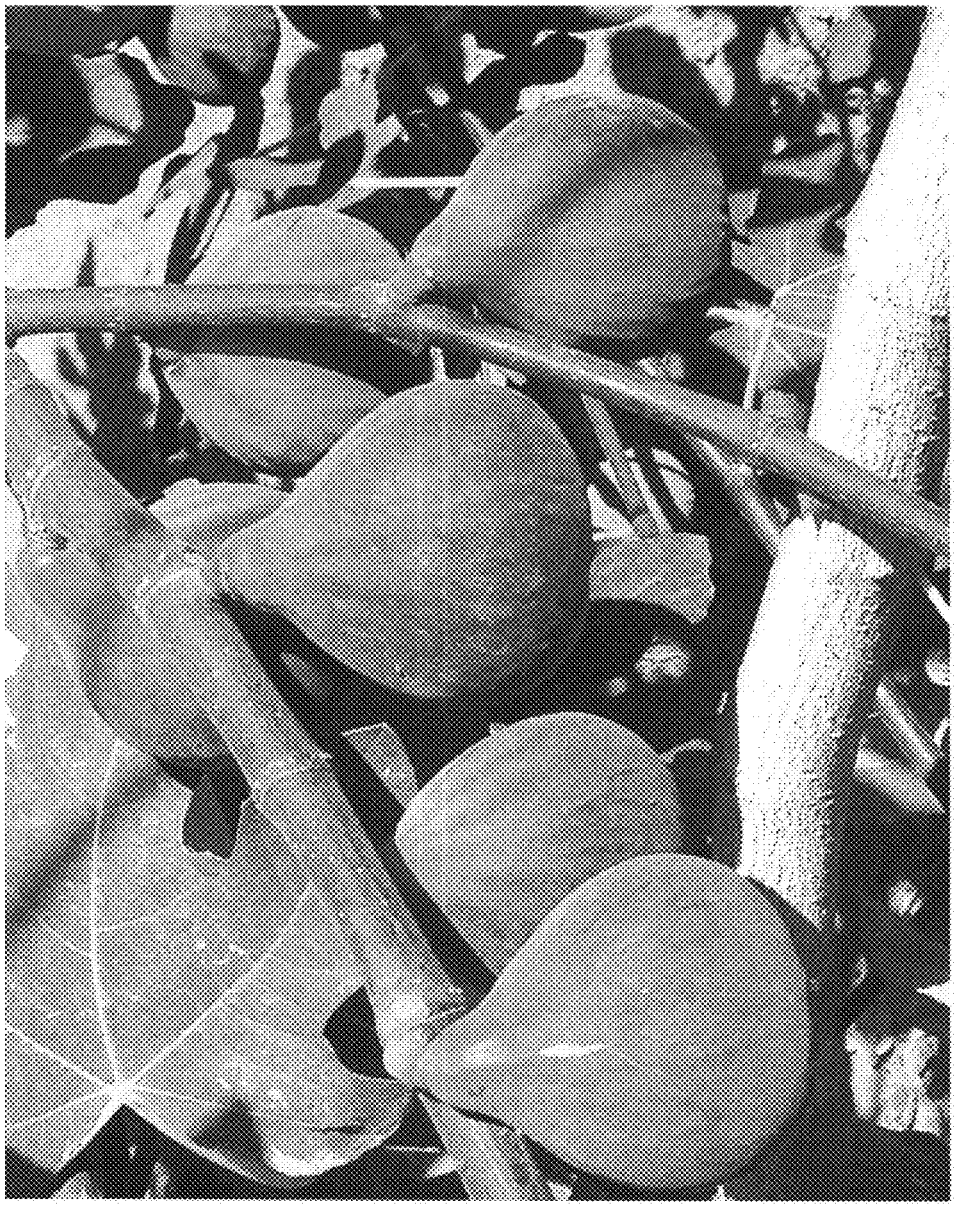
FIG. 2 is a close up of the fruit of the second or main crop produced by the present variety of fig tree at commercial maturity.
Figure 3:
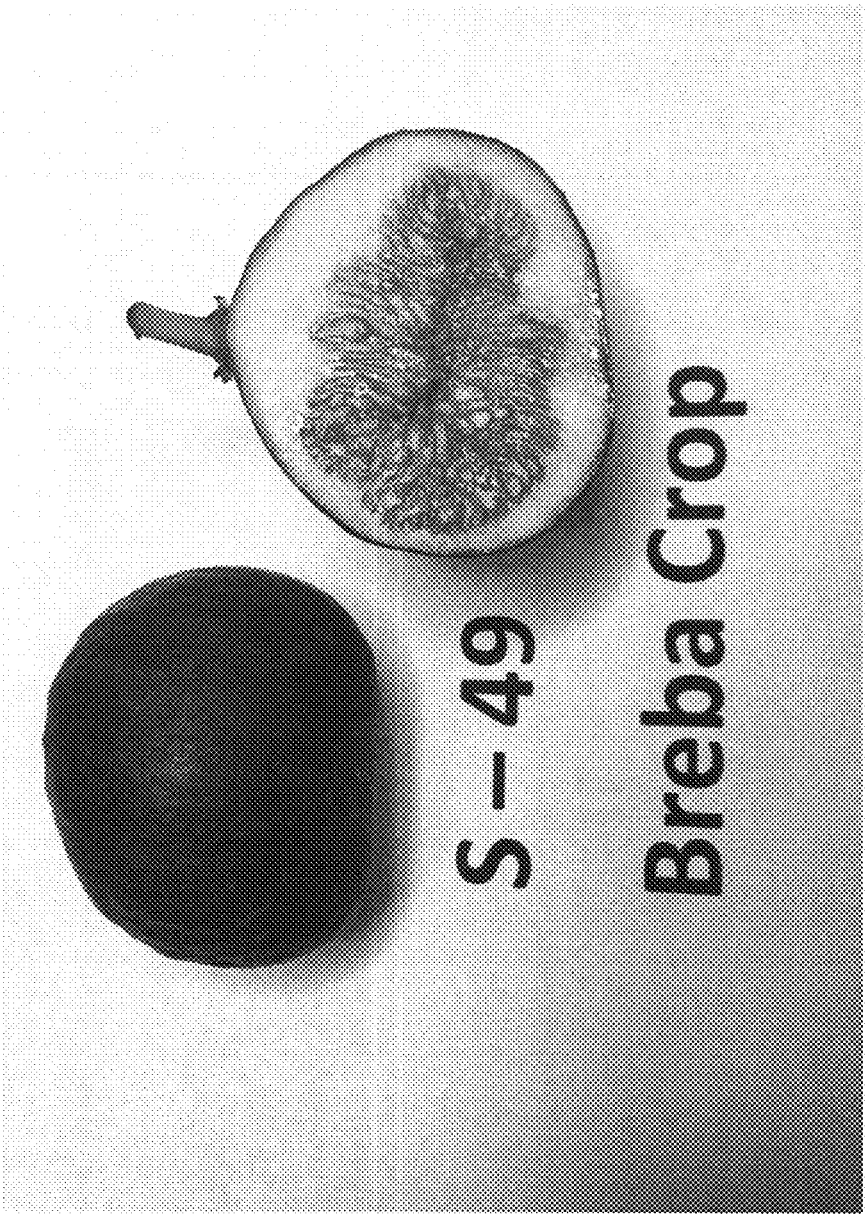
FIG. 3 depicts the fruit characteristics of the first, or breba crop of the present variety.
Figure 4:
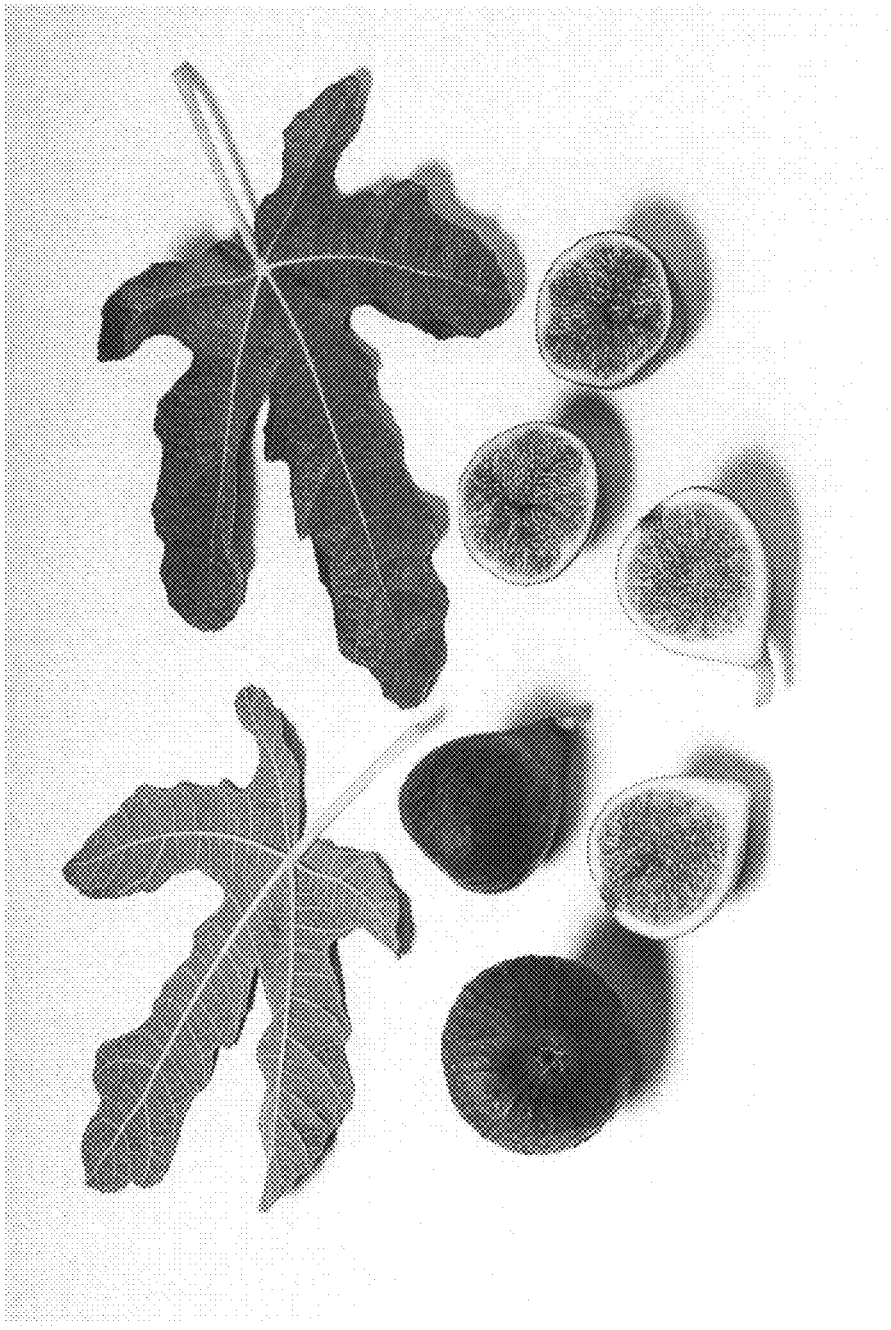
FIG. 4 displays several fruit of the present variety showing the external coloration and internal characteristics thereof. Additionally, sample vegetation showing the dorsal and ventral coloration thereof can be seen.

The colors in the enclosed photographs are nearly as true as is reasonably possible in color photographs of this type. However, due to chemical development processing, and printing, the leaves and fruit depicted in these photographs may, or may not be accurate when compared with the actual botanical specimens. For this reason, future color references should only be made to the color designations as found in The Royal Horticultural Society Colour Chart, 3$^{rd}$ Edition, and which was published in London, Great Britain in 1995. Other common color descriptions are also provided, hereinafter.

NOT A COMMERCIAL WARRANTY

The following detailed description has been prepared to solely comply with the provisions of 35 U.S.C. §112, and does not constitute a commercial warranty, [either expressed or implied], that the present variety will, in the future, display all the botanical, pomological, or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological and botanical details of this new and distinct variety of fig tree, the following has been observed during the 2015 growing season under the ecological conditions prevailing in a testing area which is located near the town of Traver, in Tulare County, Calif. All major color code designations are by reference to The Royal Horticulture Society Colour Chart, 3$^{rd}$ Edition, and which was published in Great Britain in 1995.

TREE

Size:

*Generally*.—Considered medium to small for the species. The current disclosure was taken from a seedling tree which was approximately five years old at the time of this disclosure.

Tree form:

*Generally*.—Relatively compact. Considered upright to spreading.

Hardiness: Considered hardy under normal San Joaquin Valley environmental condition.

Productivity: Productive and considered a regular bearer.

Tree height:

*Generally*.—For the present five-year old seedling, The observe tree height was approximately 6 ft. when measured during the 2015 growing season. New growth during the 2015 growing season totaled about 1.5 to about 2.5 ft.

Tree width: Approximately 10.5 ft.

Tree spacing:

*Generally*.—Originally the row spacing was approximately 18 ft. when measured from row to row. However, the tree spacing within a row has been recently modified so that a distance of about 6 ft. between the trees is now maintained.

Fig type:

*Generally*.—Considered "common" or "persistent", that being, the present fig tree variety does not need to be pollinated [caprified] in order to develop and mature fruit.

TRUNK AND SCAFFOLDS

Trunk size: About 10.5 cm. in diameter when measured at a distance of about 10 cm. from the top of the soil surface.

Trunk color: Gray [Fan 4-Sheet 201b].

Bark surface texture: Considered slightly roughened, and having low, relatively fine striations. Small scattered lenticels are also observed.

Lenticel form: Flattened, and oval. The lenticels range in size from about 1 to 3 mm. in width; and about 1 mm. in height.

Lenticel surface texture: Calloused and having a brown color, [Fan 4-Sheet 174B].

Scaffolds:

*Generally*.—Several scaffolds arise from the trunk, and range in diameter from about 2.7 to about 4 cm. when measured basally.

Scaffold surface texture: Roughened, and having longitudinal striations.

Scaffold lenticels:

*Generally*.—Similar to that seen on the trunk.

Scaffold surface color: Gray [Fan 4-Sheet 201A].

Secondary branches:

*Generally*.—These branches arise from the scaffolds and are quite variable in size. The stronger, secondary branches range in size from about 12 to about 14 mm. in diameter when measured basally.

Secondary branch surface appearance: The branch surface appears somewhat striated, longitudinally, and futher has a dark brown surface color [Fan 4-Sheet 200C].

Secondary branch lenticels: Numerous lenticels are present, and further have a light tan color [Fan 4-Sheet 165C].

Secondary branch surface texture: Pubescent. The pubescence is very short and fine.

Secondary branch distal coloration: Near the end of the smaller shoots the branch retains a green coloration, [Fan 3-Sheet 144C]. These green surfaces also have a very short, fine pubescence.

Internode length: Quite variable, from about 2.0 to about 6.0 cm. when measured near the shoot tips; and about 5.8 to about 9.7 mm. when measured in the median area of the branch.

Tip buds:

*Shape*.—Conical, and having attenuated tips.

Tip bud color: Light green [Fan 3-Sheet 145B] during the growing season.

Bud tip vertical angle: Generally this can vary from vertical to oblique at the branch end.

LEAVES

Leaf size:

*Generally*.—Considered large in size, and average in thickness. The following leaf measurements were taken from leaves growing at, or below, mid-shoot, and on vigorous, current season's growth.

Leaf width: About 16.5 to about 20.5 cm.

Leaf length: About 15.5 to about 19 cm. not including the petiole.

Surface texture, upper and lower surfaces: Pubescent. The leaf pubescence on the upper surface is short in height, and stiff. The pubescence on the lower surface is short in height, but relatively soft and velvety.

Leaf surface appearance: Generally dull in reflectance.

Leaf form:

*Generally*.—The leaves of the present variety of fig tree are usually palmately lobed. Typically five lobes are present.

Lobe form:

*Linear*.—Further the leaf base is frequently calcarate in form.

Leaf sinuses:

*Generally*.—Relatively deep, and the sinus bottoms can range from a U to a V shape, and at times a W-shape at the bottom appears.

Leaf veins:

*Generally*.—Considered very prominent on the lower leaf surface, and less so on the upper surface of the leaf. The leaf veins on both the upper and lower surfaces of the leaf are highly pubescent.

Leaf margins:

*Generally*.—Considered somewhat irregular, and at times, somewhat scalloped in form. The leaf margins may, at other times, appear crenate. Very large and broad crenations can be present.

Inner lobe margins:

*Form*.—Linear.

Leaf and vein color: The upper leaf surfaces are a dark green color, [Fan 3-Sheet 137C]. The lower leaf surface has a somewhat lighter green color [Fan 3-Sheet 138B].

Leaf vein color: Green [Fan 3-Sheet 145C].

Leaf petiole length: About 7.7 to 9.5 cm.

Petiole thickness: Variable, from about 5 to 6 mm. in diameter when measured, basally.

Petiole surface texture: A short, fine pubescence is present.

Petiole color: A light yellow-green [Fan 3-Sheet 154C].

FRUIT FLOWERS

Generally: The present variety of fig tree produced many, very small pedicellate fig flowers within each fig fruit, and on the inner surface of the hollow fig receptacle known as a synconium. These synconia are pollinated by a small fig wasp, *Blastophaga psenes* L. This pollination occurs as each of the fig fruit initiates along the expanding shoot throughout the growing season. These tiny flowers become receptive to pollination when the synconium is about 1 to 2 cm. in diameter. The florets which are produced have a 5-part perianth, and are unisexual, and further have either a long-styled or short-styled pistillate flowers. In this regard, four types of fig trees have been horticulturally identified. Firstly, the caprifig is a primitive type of cultivated fig tree, and where the above-identified fig wasp accomplishes its life cycle. This type of fig tree is the only type that sheds pollen. The fruit it produces most frequently is inedible. A second type of fig tree is the 'Smyrna' fig tree. This type of fig tree only matures after pollination by the fig wasp. After pollination the presence of fertile embryos stimulates the figs to remain on the tree and to ripen. Those skilled in the art will recognize that if this type of fig tree is not pollinated, the fruit begins to grow, but then, at the size of an inch, or perhaps less in diameter, the fruit shrivels, and then falls from the tree. A third type of fig tree has been identified and is considered to be a "common" or "persistent" fig tree. This type of fig tree does not need to be pollinated by the fig wasp in order for the fruit to remain on the tree and to come to full commercial maturity. The fourth type of fig tree is the 'San Pedro' fig tree. This type of fig tree is an intermediate type of fig tree, and where the first [breba] crop is persistent, but the second, or main crop is of the 'Smyrna' type, and needs pollination to mature the crop so that it may be harvested. The present variety of fig tree, 'S-49', is of the "common" or persistent type, and it does not need to be pollinated to set and mature a breba and second crop of fruit. The color of the flowers is not distinctive of the present variety.

Fruit description: The following descriptions which are provided include both the first and second crops of the new fig tree 'S-49'. It should be understood, and within the commercial fig industry, the first crop of figs harvested is known as the 'breba' crop. The breba crop is produced on the previous season's growth. This first crop is usually light in volume, and the fruit is usually larger in size. Depending upon the ambient environmental factors, the fruit size, and crop volume, may vary considerably from year to year. This breba crop matures early in the season, usually in early June, under the prevailing environmental conditions found in the San Joaquin Valley of Central California. The second, or "main" crop is usually high in volume, and makes up the bulk of the commercial production realized from these fig trees. The second or main crop usually produces smaller sized fruit in relative comparison to the breba crop and, depending on the variety of fig tree being harvested, begins to mature in mid-July to early August under the environmental conditions which are typically experienced in the San Joaquin Valley of Central California. Each crop of the same variety may have some differences of appearance, flavor and quality as well as volume. What follows are separate descriptions for each crop [breba and main] of the new variety fig tree variety 'S-49'.

BREBA [FIRST CROP] FRUIT

Maturity when described tree ripe, and ready for commercial harvesting: Jun. 8, 2015 under the ecological conditions prevailing in the San Joaquin Valley of Central California.

Harvesting dates: About 4 June through 15 June in 2015.

Fruit size: Generally considered large for the species.

Fruit width: About 56 mm.

Fruit length: About 48 mm.

Fruit weight: Can vary significantly from about 55 to over 70 grams. per fruit.

Fruit form: Spherical.

Fruit neck:

*Generally*.—This feature is considered very low, but more frequently, there is no neck present at all.

Fruit stem:

*Length*.—About 13 mm.

Fruit stem:

*Thickness*.—About 6 mm. in diameter, when measured basally.

Fruit stem color: Yellow-green, [Fan 3-Sheet 152D]. Occasionally the stem is a lighter, yellow-green colo, [Fan 3-Sheet 153A].

Color:

*Stem base*.—The stem base can be overlaid with a light purplish blush [Fan 4-Sheet 177C].

Bracts: Three bracts are usually present on the stem, and are appressed relative to the fruit.

Bract size: These individual bracts range in size from about 3 to about 4 mm. in height, and about 5 to 6 mm. in width.

Bract color: Greenish-yellow [Fan 3-Sheet 153D].

Fruit ribs:

*Generally*.—The ribs are present, and are disposed generally, longitudinally, on the fruit, and further extend from the fruit stem, and down to the fruit eye. The ribs are not very prominent.

Fruit rib surface texture: Smooth.

Fruit rib color: Dark purple [Fan 4-Sheet 187A].

Fruit eye:

*Generally*.—The eye of the fig is of medium size, and averages about 4 mm. in diameter.

Fruit eye surface texture: Many scales are present, and are located around the perimeter of the eye, and extend down, and block the entrance into the fig ostiole.

Fruit skin:

*Generally*.—Considered moderately thick, and durable.

Fruit skin surface texture: Moderately glossy.

Fruit skin pubescence: Present but considered extremely short and scattered across the surface of the fruit skin. No skin tearing or renting is present.

Fruit skin color:

*Generally*.—A very dark purple [Fan 4-Sheet 187A]. This dark purple color appears especially over the fruit shoulder area. A slightly lighter color is seen basally. Occasionally, green areas can be seen near the stem [Fan 4-Sheet 195A].

Fruit skin flecking: Flecking appears throughout the fruit skin, and is most prevalent over the fruit shoulder area.

Fleck size: Fleck size is usually small, and can vary from about 0.5 to about 2 mm. in diameter.

Fleck color: Usually a very light tan color [Fan 4-Sheet 157C].

Fig meat:

*Generally*.—Considered moderately thick, and ranging in thickness from about 3 to about 5 mm., at its thinnest point, and about 8 to 9 mm. at its thickest point, and which is near the stem of the fruit. The fig meat is tender, and relatively sweet in flavor. The fig meat color is nearly white [Fan 4-Sheet 155B].

Fig pulp:

*Generally*.—The fig pulp usually fills the center of the synconium completely. The upper and lower pulp surfaces meet at an interface at the center of synconium.

Fig pulp color: Strawberry-red, [Fan 1-Sheet 43B]. Occasionally a lighter red color is seen [Fan 1-Sheet 43C], and there is a moderate amount of color variation therebetween. The fig pulp is relatively fine grained.

Seeds:

*Generally*.—Many seeds are present in the fruit pulp.

Seed shape: The seeds range in shape from oval to globose in form.

Seed size: About 1 mm. in diameter.

Seed color: Tan [Fan 4-Sheet 164B].

Fig flavor:

*Generally*.—Considered very good, sweet and rich and further having a slight acidity.

Usage:

*Generally*.—A fresh market fig for both local and long distance markets.

DESCRIPTION OF SECOND [MAIN] CROP

Date of description: This description was taken on 27 Jul. 2015. Further, this description was prepared from a tree growing in Traver, Calif. As a general matter, the crop size was above average, and the second crop was borne on current season's growth. The range of maturation of the fruit varied from tree-ripe to totally immature. It should be understood that the second crop was classified as the "common" or "persistent" type. This crop does not need pollination [caprification] to set, and develop a mature fruit.

Fruit maturity:

*Generally*.—The fruit of this 'S-49' fig tree began to mature in mid-July, 2015 [19 Jul. 2015]. It should be understood that the 2015 growing season was approximately 10 days earlier than what is considered average. In this regard it should be understood that the figs are produced successively on the axils of actively growing shoots from about mid-July, until late in the fall. The commercial production of figs terminates when the shoots stop elongating, and which usually occurs, due to heat, or drought, or further when other ambient environmental factors such as fog, rain, frost, etc. makes the fruit unsalable.

Fruit size:

*Generally*.—Typically large in size and abundant. The fruit size is variable.

Fruit length: About 51 to 65 mm. including the stem.

Fruit width: About 43 to about 60 mm.

Fruit weight: Variable from about 45 to 95 grams. A high percentage of the early, second crop, weighs more than 50 grams. per fruit.

Fruit form: Variable from spherical, with a medium to short neck, to spherical with almost no neck.

Fruit neck:

*Generally*.—The fruit neck varies from short, to elongated, and having a length of about 5 to about 14.1 mm.

Neck color: Lighter than the color of the body of the fruit, and which ranges from a red-purple color, [Fan 2-Sheet 58A], to a lighter red-purple color [Fan 2-Sheet 59D]. Occasionally areas on the neck of the fruit show a yellowish-green ground color, [Fan 3-Sheet 153C].

Fruit stem:

*Length*.—Medium, and ranging in length from about 6 to about 15 mm.

Fruit stem:

*Diameter*.—About 5 mm. when measured, basally.

Fruit stem color: Bronze-yellow [Fan 3-Sheet 153D], and occasionally greenish-yellow [Fan 3-Sheet 151A]. From time-to-time, the fruit stem is overlain with a reddish-purple coloration which is variable from a light red color, [Fan 2-Sheet 58D], to a darker red purple color [Fan 2-Sheet 58A].

Fruit stem surface texture: Moderately pubescent, and having very short and fine hairs. Occasionally, several irregular-shaped bracts are present. If bracts are found they are usually three in number, and further surround the stem apex, and where the stem adjoins the fruit neck.

Bract color: Variable, and having mixed colorations of red-purple, [Fan 2-Sheet 60D]; and yellow-green, [Fan 3-Sheet 151C].

Fruit ribs:

*Generally*.—The ribs are low, and not very prominent. The ribs are also continuous, and extend, longitudinally, from the top of the neck, and down to the eye of the fruit. The ribs are regular in occurrence.

Fruit rib color: Considered to have a darker color than the body of the fruit, and which varies from a reddish-purple color, [Fan 4-Sheet 181A], and intensifies to a dark purple color, [Fan 4-Sheet 187A], with advancing maturity.

Fruit eye:

*Generally*.—Considered small, and relatively tight.

Fruit eye diameter: Ranging from 0 to about 0.4 mm.

Eye splitting: This can occur especially when irrigation of the trees is considered excessive.

Fruit eye surface texture:

*Generally*.—External scales surround the eye and are small in size, conic in form, and further appressed relative to the fruit.

External scale color: Variable from a light red-purple [Fan 3-Sheet 182A] to a darker purple [Fan 4-Sheet 187A].

Fruit skin:

*Generally*.—Considered moderately thick, and durable, and covered with a light grayish bloom. A small amount of skin renting is present when the fruit is grown under careful irrigation practices.

Fruit skin surface texture: A short, very fine pubescence is scattered across the skin surface. The fruit skin peels easily from the fruit at full commercial maturity.

Fruit skin color: Variable, from a light red-purple color, [Fan 4-Sheet 182A], at commercial maturity, to a dark purple color, [Fan 4-Sheet 187A], with advancing maturity. Some greenish color can appear around the neck, at the early commercial maturity stage, [Fan 3-Sheet 153C].

Fruit skin flecking: Skin flecking is present on the skin surface, and most frequently is found on the lateral surfaces.

Flecking density: From nearly absent, to moderately scattered.

Fleck size: Small and most frequently oval in shape. Approximately 1 mm. in size when measured in the horizontal plane, and about 1.5 to about 2 mm when measured in the vertical plane.

Fleck color: The flecks are lighter in color, [Fan 2-Sheet 62D].

Fig meat:

*Generally*.—The fig meat is located just under the skin surface, and is moderately thick, about 5 to 6 mm., when measured along the lateral surfaces, and from about 5 to 7 mm. when measured near the fruit base, and the apex. The Fig meat is white in color [Fan 4-Sheet 155A], and moderately firm, and sweet.

Fig pulp color: Generally a dark strawberry-red color, [Fan 4-Sheet 180B], and becoming darker in color with advancing maturity, [Fan 4-Sheet 181B]. The fig synconium is well-filled with pulp. The center of the synconium can vary from completely filled to slightly open in the center. The texture of the pulp is finely grained.

Fig seeds:

*Generally*.—Considered abundant within the pulp, and varies from oval to ovate in form.

Fig seed diameter: Variable from 1 to about 1.8 mm.

Seed color: Light brown, [Fan 4-Sheet 165C].

Fig flavor:

*Generally*.—Very good, and considered both sweet and rich.

Fruit usage: The fruit of the 'S-49' is primarily suited for the fresh market. The fruit produced by the 'S-49' fig tree may also have a commercial potential for the dry market, but this potential has not been fully explored.

COMPARISON WITH OTHER KNOWN VARIETIES

Generally: In comparison to the two closest known varieties, those being the 'Desert King' fig tree, and the 'CA Brown Turkey' fig tree [both unpatented], the following distinctions are noted. As I have previously described, the 'Desert King' fig tree is the female parent of the new variety 'S-49'. It is substantially different than the 'S-49' fig tree in that it produces a green-skinned fruit, rather than the dark purple-skinned fruit produced by the 'S-49' fig tree. Additionally, the 'Desert King' fig tree produces fruit which has a fairly open eye unlike the more closed eye as displayed by the fruit of the new variety of fig tree. In addition, the 'Desert King' fig tree is a 'San Pedro' type of fig tree that needs to be pollinated in order to set a second crop. On the other hand, the present variety of fig tree needs no pollination to set fruit either the breba, or the second crop. In comparison to the 'CA Brown Turkey' fig tree variety, this fig tree variety produces a purple-skinned fig fruit that makes up a substantial percentage of the fresh fig production produced by the state of California. As earlier discussed, the caprifig tree variety '91 C' [unpatented] is the pollen [male parent] of the 'S-49' fig tree. There are some similarities between the 'S-49' fig tree and the 'CA Brown Turkey' fig tree including the tree precocity, and the overall fruit production. Still further the general fruit color and fruit size remain somewhat similar. The chief differences between these two varieties relates to the tree size, fruit coloring near the neck, the fruit interior characteristics, and the fruit eye. In relative comparison to the 'CA Brown Turkey' fig tree, the current, new variety of fig tree appears to have a tree size which is somewhat smaller than that displayed by the 'CA Brown Turkey'. Still further, the fruit color of the 'S-49' fig tree, appears to be more violet-purple in color than the same color which is displayed by the 'CA Brown Turkey' fig tree, especially when this is viewed near the neck and shoulders of the fruit. Further, the fruit neck of the 'CA Brown Turkey' fig tree often displays patches of yellow-brown color. Moreover, the interior pulp of the 'CA Brown Turkey' fruit often has a hollow area in the center of the fruit, while the center of the fruit produced by the 'S-49' fig tree is more closely closed, and filled. Additionally, the fruit of the 'S-49' fig tree has a smaller fruit eye than that which is seen on the fruit of the 'CA Brown Turkey' fig tree especially under careful irrigation practices. The fruit produced by both the 'S-49' fig tree, and the 'CA Brown Turkey' fig tree are acceptable commercially, but the fruit produced by the 'S-49' fig tree seems to develop a sweeter flavor at an earlier stage of maturity.

Although the new variety of fig tree possesses the described characteristics when grown under the ecological conditions prevailing in the San Joaquin Valley of Central California, it should be understood that variations of the usual magnitude and characteristics incident to changes in growing conditions, fertilization, pruning and pest control, as well as horticultural management practices, are to be expected.

Having thus described and illustrated my new variety of fig tree, what I claim is new, and desire to secure by Plant Letters Patent is:

1. A new and distinct variety of fig tree as substantially illustrated and described, and which is characterized principally as the novelty by bearing a large red-purple to purple-skinned fig of the common type, and which further has fruit pulp which has an attractive strawberry-red color, a fine texture, and a sweet and rich flavor, and which further is ripe for a second crop harvesting, and shipment, during late July and early August, under the ecological conditions prevailing in the San Joaquin Valley of Central California.

* * * * *